(12) United States Patent
Siversson

(10) Patent No.: US 7,674,630 B2
(45) Date of Patent: Mar. 9, 2010

(54) METHOD AND DEVICE FOR SEPARATING PARTICLES

(75) Inventor: Carl Siversson, Helsingborg (SE)

(73) Assignee: Spectronic AB, Helsingborg (SE)

( * ) Notice: Subject to any disclaimer, the term of this patent is extended or adjusted under 35 U.S.C. 154(b) by 328 days.

(21) Appl. No.: 11/663,574

(22) PCT Filed: Sep. 23, 2005

(86) PCT No.: PCT/EP2005/054794

§ 371 (c)(1),
(2), (4) Date: Mar. 23, 2007

(87) PCT Pub. No.: WO2006/032703

PCT Pub. Date: Mar. 30, 2006

(65) Prior Publication Data

US 2008/0217259 A1   Sep. 11, 2008

(30) Foreign Application Priority Data

Sep. 24, 2004   (SE) .................................. 0402312

(51) Int. Cl.
*G01N 1/18* (2006.01)
(52) U.S. Cl. ........................................ 436/177; 210/748
(58) Field of Classification Search .................. None
See application file for complete search history.

(56) References Cited

U.S. PATENT DOCUMENTS 6,332,541 B1   12/2001   Coakley et al.

FOREIGN PATENT DOCUMENTS

| EP | 0773055 A2 | 5/1997 |
|----|------------|--------|
| WO | WO-02/29400 A2 | 4/2002 |
| WO | WO-02/072235 A1 | 9/2002 |
| WO | WO-2003/102737 A2 | 12/2003 |

OTHER PUBLICATIONS

Mandralis et al., "Enhanced synchronized ultrasonic and flow-field fractionation of suspensions", Ultrasonics, vol. 32, No. 2 (1994).*
"International Application Serial No. PCT/EP2005/054794, International Preliminary Report on Patentability completed Dec. 28, 2006", 7 pgs.
"International Application Serial No. PCT/EP2005/054794, International Search Report mailed Feb. 22, 2006", 2 pgs.
"International Application Serial No. PCT/EP2005/054794, Written Opinion mailed Feb. 22, 2006", 7 pgs.

* cited by examiner

*Primary Examiner*—Yelena G Gakh
*Assistant Examiner*—Dirk Bass
(74) *Attorney, Agent, or Firm*—Schwegman, Lundberg & Woessner, P.A.

(57) ABSTRACT

The invention relates to a method and a device for separating particles using ultrasonic standing waves which are switched between two different frequencies. A second order harmonic standing wave is used together with the fundamental standing wave. If the particles are exposed to the fundamental standing wave, the forces act to collect particles at the center. If the particles are exposed to the second order harmonic standing wave, the forces act to collect particles at the two pressure nodes at the sides. By switching the frequency between the second order harmonic standing wave and the fundamental standing wave, particles with different properties will be exposed to different accelerations and are separated into two streams.

9 Claims, 4 Drawing Sheets

METHOD AND DEVICE FOR SEPARATING PARTICLES

RELATED APPLICATIONS

This application is a nationalization under 35 U.S.C. 371 of PCT/EP2005/054794, filed Sep. 23, 2005 and published as WO 2006/032703 A1, on Mar. 30, 2006, which claimed priority under 35 U.S.C. 119 to Sweden Application No. 0402312-3, filed Sep. 24, 2004; which applications and publication are incorporated herein by reference and made a part hereof.

FIELD OF INVENTION

The present invention relates to a method and a device for separating particles, and more particularly separation of particles using ultrasonic standing waves which are switched between two different frequencies. Particles with different properties will be exposed to different accelerations due to acoustic radiation pressure and are separated into two streams.

STATE OF THE ART

The theory behind the forces acting on particles suspended in a medium in an ultrasonic standing wave has been known for some time. If a standing wave is induced into a medium where a small particle is suspended the particle will be exposed to an acoustic radiation force. The force acting on the particles is a function of the position in the channel relative to a pressure node. By combining this fact with laminar flow in microchannels, particles can be collected at and separated from the pressure nodes. In the fundamental standing wave (first order resonant frequency) the force is directed towards the centre where the pressure minimum is located as discussed below with reference to FIGS. 1AB and 2AB. Such standing waves can be created in a channel with parallel side walls. This phenomenon has previously been utilized for particle separation in microfluidic systems. Reference is made e.g. to WO 02/072235. In the previous method, the fact that the force F has different signs, i.e. directions, for different particles was exploited. Here, some particles were collected at and other particles separated from the pressure node. The difference in signs is mainly dependent on whether the particle has higher or lower density than the surrounding medium. However, with this method it was not possible to separate particles that were exposed to forces acting in the same direction, even if the forces had different magnitudes.

SUMMARY OF THE INVENTION

In the present invention, a second order harmonic standing wave is used together with the fundamental standing wave. If the particles are exposed to the second order harmonic standing wave, the force acts towards two pressure nodes at the sides. By switching the frequency between the second order harmonic standing wave and the fundamental standing wave, particles may be separated and collected at the different sets of pressure nodes.

In a first aspect, the invention provides a method for separation of particles of a particle mixture suspended in a medium, comprising the steps of:

subjecting a chamber containing the medium to ultrasound generating a first ultrasonic standing wave at a first frequency having first pressure nodes;

placing the particle mixture in the chamber, so that a concentration of the particle mixture is placed at or in the vicinity of a first pressure node of the ultrasonic standing wave at said first frequency or anywhere between the first pressure node and a wall of the chamber;

switching the frequency of the ultrasonic standing wave to a second frequency generating a second ultrasonic standing wave having at least one second pressure node, so that a first set of particles of the particle mixture is experiencing a smaller acceleration towards said second pressure node, and a second set of particles of the particle mixture is experiencing a greater acceleration towards said second pressure node;

maintaining the second frequency during a time duration t2 and with an amplitude a2, allowing the first set of particles of the particle mixture to travel a smaller distance, and the second set of particles of the particle mixture to travel a greater distance;

switching back to the first frequency;

wherein the first distance is so small that the first set of particles of the particle mixture is experiencing a greater acceleration towards the first pressure node, and the second distance is so great that the second set of particles of the particle mixture is experiencing a smaller acceleration towards the first pressure node;

maintaining the first frequency during a time duration t1 and with an amplitude a1, allowing the first set of particles of the particle mixture to travel back towards the first pressure node, while the second set of particles of the particle mixture is not allowed to travel a significant distance;

repeatedly switching the ultrasonic standing waves between the first and second frequencies with a duty cycle involving their respective time durations t1 and t2 and amplitudes a1 and a2, so that a substantial part of the first set of particles of the particle mixture is collected at the first pressure node, and a substantial part of the second set of particles of the particle mixture is collected at the second pressure node.

In a second aspect, the invention provides a device for separation of particles of a particle mixture suspended in a medium, comprising:

a chamber for containing the medium;

an ultrasound transmitter for generating ultrasonic standing waves in said chamber;

wherein the ultrasound transmitter is arranged to switch repeatedly the frequency of the ultrasonic standing wave between a first frequency having first pressure nodes and a second frequency having at least one second pressure node; the ultrasonic standing wave at the first frequency having a time duration t1 and an amplitude a1, and the ultrasonic standing wave at the second frequency having a time duration t2 and an amplitude a2.

The invention is defined in claims 1 and 11, while preferred embodiments are set forth in the dependent claims.

BRIEF DESCRIPTION OF THE DRAWINGS

The invention will be described in detail below with reference to the appended drawings, in which.

DETAILED DESCRIPTION OF PREFERRED EMBODIMENTS

As mentioned in the introduction, the present invention relates to a method and device for separation of particles with different sizes, compressibilities, densities or generally different properties suspended in a fluid. The method utilizes ultrasonic standing waves at a fundamental resonant frequency and at a second order harmonic frequency, preferably in combination with the laminar flow properties of a microchannel. Particles with different properties e.g. density, suspended in a medium, enter a channel through side inlets and a particle-free medium enters via a centre inlet, forming three laminated streams. By sequentially switching between the fundamental and the second order harmonic standing waves, higher density particles can be positioned close to the pressure node of the fundamental standing wave, while the lower density particles are positioned close to the pressure nodes of the second order harmonic standing wave. The channel is split into three exit channels, separating the streams of high-density and low-density particles.

If a standing wave is induced into a medium where a small particle is suspended the particle will be exposed to an acoustic radiation force according to the theory presented by Yosioka K. and Kawasima Y.; Acustica 5, pp 167-173, (1955).

$$F_y = -\left(\frac{\pi P_0^2 V_o \beta_w}{2\lambda}\right) \cdot \left(\frac{5\rho_c - 2\rho_w}{2\rho_c + \rho_w} - \frac{\beta_c}{\beta_w}\right) \cdot \sin\left(\frac{4\pi z}{\lambda}\right) \quad (1)$$

$V_c$ is the volume of the particle. $P_0$ is the pressure amplitude. Z is the particle position. The density of the medium and the particle are denoted $\rho_w$ and $\rho_c$ respectively and the corresponding compressibilities $\beta$ and $\beta_c$. From this expression and the basic physic formula ($F=m_c \cdot a$), where $m_c$ is the mass of the particle, the acceleration of the particle may be calculated. When the particle is moving, there is also a retarding force depending on the viscosity of the medium, the speed, and the volume and shape of the particle.

It then becomes clear that the acceleration, and thus the lateral speed and movement, of a small particle is a function of many variables, among which the most important are the volume, density and compressibility of the particle.

Figure 1A:
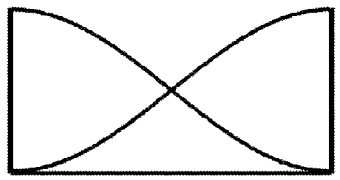
FIGS. 1A and 1B are diagrams of pressure nodes in a chamber with standing acoustic waves at a fundamental frequency and at a second order harmonic frequency, respectively.
Figure 1B:
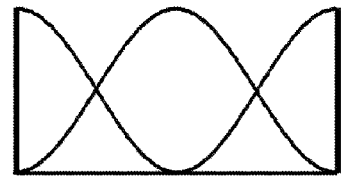

FIGS. 1A and 1B illustrate fundamental and second order harmonic standing waves, respectively, in a chamber or channel. The X-axis denotes spatial position in channel. The Y-axis denotes standing wave pressure.

Figure 2A:
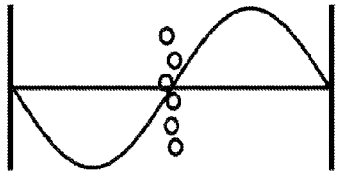
FIGS. 2A and 2B are diagrams of the acoustic radiation force in a chamber with standing acoustic waves at a fundamental frequency and at a second order harmonic frequency, respectively.
Figure 2B:
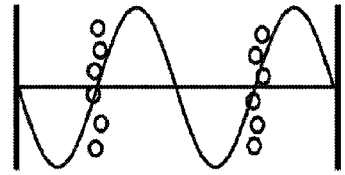

FIGS. 2A and 2B also illustrate fundamental and second order harmonic standing waves, but the Y-axis denotes the force acting on a suspended particle. Particles are gathered at the pressure nodes, assuming that a positive force means that the force on the particle is directed to the left in the diagram.

As may be inferred by studying FIGS. 1A and 2A, at the fundamental standing wave, the forces act to collect the particles at the pressure node in the centre. As shown in FIGS. 1B and 2B, at the second order harmonic standing wave, however, there are two pressure nodes. In the vicinity of and closer to the wall of each pressure node the forces act to collect the particles, but in the centre of the chamber, there is a force minimum. Thus, only weak the forces act to separate particles from the centre and accelerate them to the lateral pressure nodes. This is exploited in the present invention. By switching between fundamental and second order harmonic standing waves, the faster moving particles may be moved from the lateral pressure nodes and collected at the centre, while the slower moving particles may not escape from the forces acting to collect the particles in the lateral pressure nodes.

As mentioned above, it can be shown that particles with different size, density, compressibility or other variables based on their physical properties, are affected by different accelerations when they are exposed to the same standing wave. This is also consistent with the force equation (1). Thus, different particles will be translated laterally at different speeds. For instance, if two particles have the same density, the larger particle will be exposed to the greater acceleration. If two particles have the same volume, the particle having the higher density will be exposed to the greater acceleration. By rapid switching between the fundamental and the second order harmonic standing waves, e.g. high-density and low-density particles can be separated laterally.

Figure 3A:
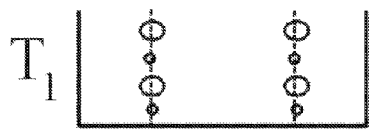
FIGS. 3A-3D are diagrams of a chamber with particles at different steps of the separation.

The present invention is explained with reference to high-density and low-density particles carried by a laminar flow in a channel. Generally, high-density particles refer to faster moving particles, and low-density particles refer to slower moving particles. When the separation starts the situation is as shown in FIG. 3A. Initially the particles are injected along the side walls of the channel. A first frequency generates a second order harmonic standing wave. All the particles are located in the vicinity of the pressure nodes or closer to the wall. $T_1$-$T_4$ indicates the time instants in the switching process. Large circles indicate large or high-density (faster moving) particles. The particles may be concentrated into these positions by subjecting the channel to a second order harmonic standing wave having lateral pressure nodes for a sufficient duration in a separate preseparation channel upstream of the separation area.

Figure 3B:
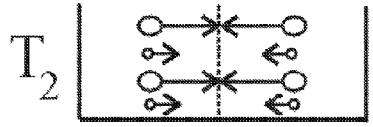

In FIG. 3B the frequency is switched to a second frequency generating a fundamental standing wave. When the fundamental standing wave is applied the particles are forced towards the centre of the channel. However, high density particles move faster towards the centre. The standing wave at the second frequency is applied for a time duration t2 and with an amplitude a2. The duration and amplitude are sufficient for the high-density particles to reach close to the centre of the separation channel. The fundamental standing wave is switched off before the low-density particles reach the centre.

Figure 3C:

In FIG. 3C the frequency is switched back to the first frequency. Thus, the second order harmonic standing wave is applied. At this point the higher density particles are not strongly affected, since they are closer to the force minimum in the centre of the second order harmonic standing wave (cf. FIG. 2B). However, the particles that never reached the centre of the channel during the fundamental standing wave cycle will, at this point, be in a position where they are exposed to a significant force moving them away from the centre of the channel and back to the lateral pressure nodes again. The standing wave at the first frequency is applied for a time duration t1 and with an amplitude a1. The duration and amplitude are sufficient for the low-density particles to reach the lateral pressure nodes. On the other hand, the duration is sufficiently short, so that the second order harmonic standing wave is switched off before the higher density particles reach the lateral pressure nodes.

Figure 3D:
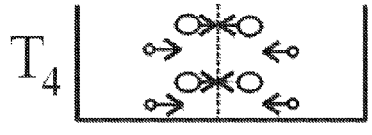

In FIG. 3D, the procedure is repeated by switching to the second frequency generating the fundamental standing wave. This time the high-density particles start from a position slightly closer to the centre of the channel, while the low-density particles start closer to the lateral positions. Then a greater part of the high-density particles will reach the centre of the channel. As this is repeated equilibrium will be reached. The higher and lower density particles are separated into two streams close to the pressure nodes of the fundamental and second order harmonic standing wave, respectively.

Generally, by repeating such a procedure particles may be separated in different flow lines based on their physical properties as manifested in their experienced different accelerations.

Figure 4:
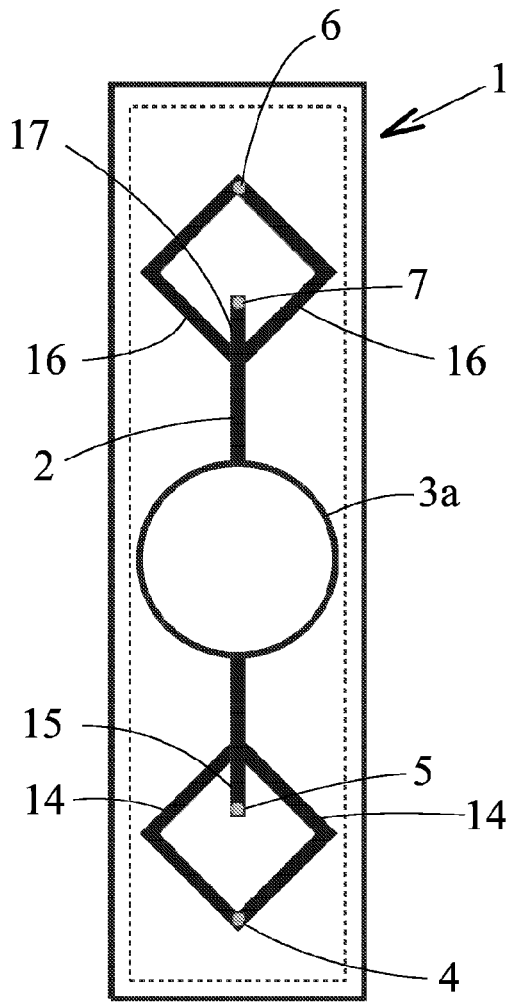
FIG. 4 is a top view of a separation device according to a first embodiment of the invention.
Figure 5:
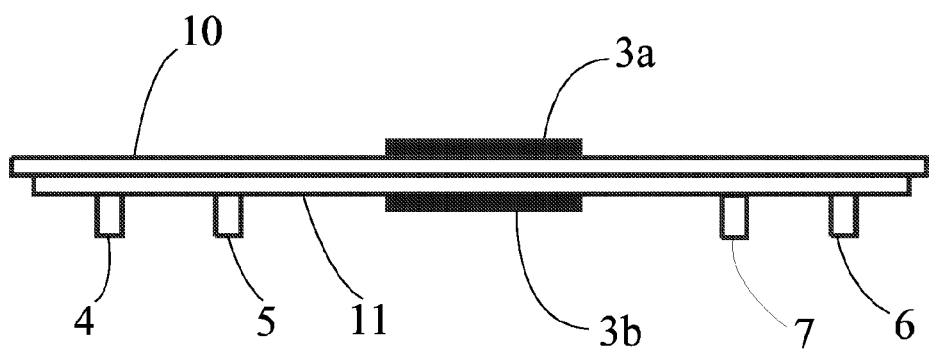
FIG. 5 is a side view of the separation device of FIG. 4.

A first embodiment of a separation device is shown in FIGS. 4 and 5, being a top view and a side view, respectively. It should be appreciated that even though the device is illustrated as having a horizontal flow, the device may have any orientation relative to gravity, since gravity has very little influence on suspended microparticles. Throughout this specification the terms horizontal, top and bottom etc are only used with reference to the drawings. The separation device 1 comprises a separation chamber or channel 2 formed in a base plate 11 with a cover 10, suitably a transparent glass lid so that the separation process may be inspected visually. The ultrasonic standing wave is generated by means of an ultrasonic transmitter, suitably a pair of a top transmitter element 3a mounted on the top side of the structure and a bottom 3b transmitter element mounted at the bottom. As is known, the ultrasonic standing wave is generated between the side walls in dependence of the existing resonance conditions, transverse to the flow direction, even though the transmitters are located at the top and bottom. The end and the beginning of the separation channel 2 are split into three entry and three exit channels. In the central entry channel 15 a medium without particles is inserted from an inlet 5. The medium may e.g. be water or saline depending on the application. In the side entry channels 14 (mixed particles inlet), a fluid with a mix of high-density and low-density particles is inserted from a common inlet 4. In the separation channel 2 separated flows of the various particles are formed gradually. FIGS. 3A-D are representative of cross sections at consecutive positions in the separation channel. In the central exit channel 17 medium with separated large particles is delivered through an outlet 7. In the side exit channels 16 medium with separated small particles is delivered through a common outlet 6. Flow connectors (not shown) are mounted on the bottom side of the structure.

In an alternative embodiment, the three entry channels are replaced by one common inlet (not shown) receiving a flow with two streams of mixed particles located at the side walls and a particle-free stream in the centre, roughly corresponding to the situation in FIG. 3A. The particles may be formed into the two streams by subjecting a preseparation chamber to a continuous second order harmonic standing wave. Such a preseparation chamber is discussed below with reference to FIG. 9 in relation to the second embodiment of the invention.

Figure 6:
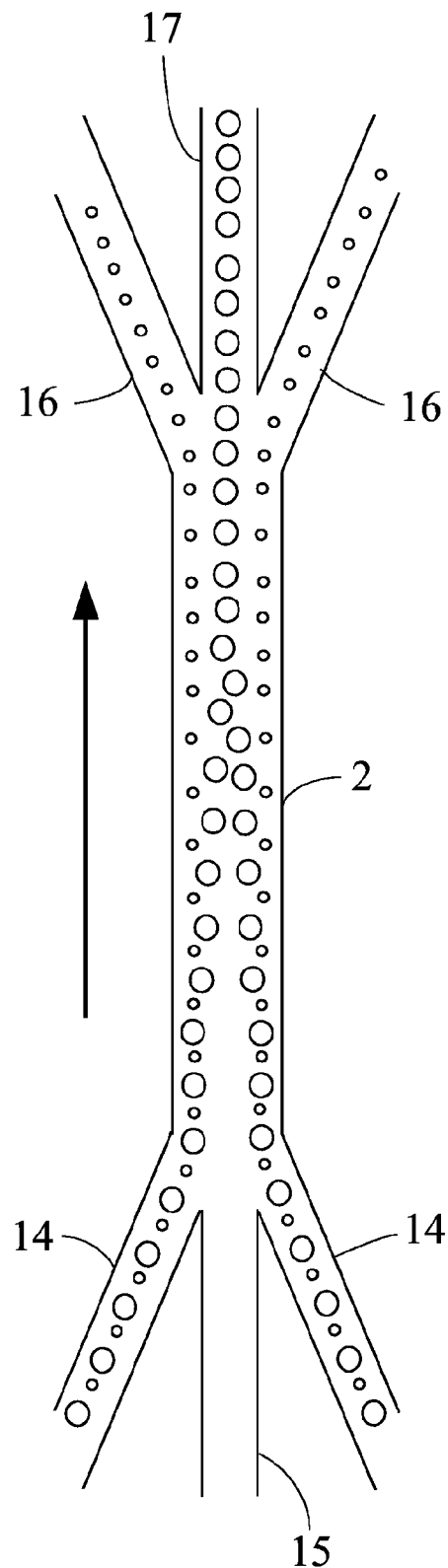
FIG. 6 is a schematic top view of a separation process where different particles are separated and directed to different outlets.

FIG. 6 shows a device with a separation channel 2 according to the invention. The flow is directed as shown by the arrow. In the side entry channels 14 a fluid with a mix of high-density and low-density particles is inserted. The particle mix is separated in two groups in the separation channel 2 when exposed to a number of switching cycles. Since the flow is laminar the large high-density particles are directed to the centre exit channel 17 and the small low-density particles are directed to the lateral exit channels 16. Different sets of particles may be directed to the different exit channels 16 and 17 by selecting a suitable duty cycle, that is adapting the durations t1 and t2. In some applications, a suitable duty cycle may be selected by visually observing the different streams directed to the exit channels 16 and 17 while trying different durations t1 and t2 until the desired separation is achieved. t1 and t2 may be set by adjusting a control panel (not shown) associated with the drive circuits of the ultrasonic transmitters. Alternatively, the duty cycle is fixed, e.g. t1=t2, and instead the amplitudes a1 and a2 of the ultrasonic waves emitted by the transmitter at the respective frequencies are adjusted to generate the corresponding translational movement to induce the desired separation.

Figure 7:
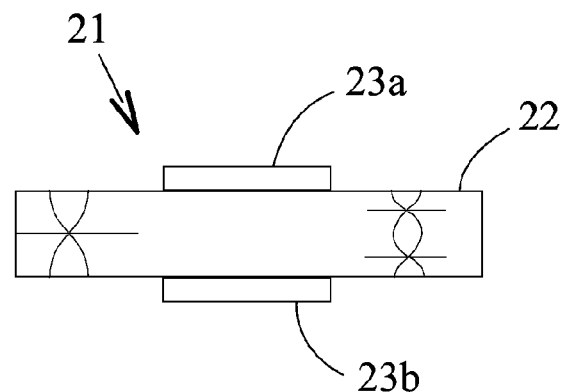
FIG. 7 is an side view of a separation device according to a second embodiment of the invention.
Figure 8:
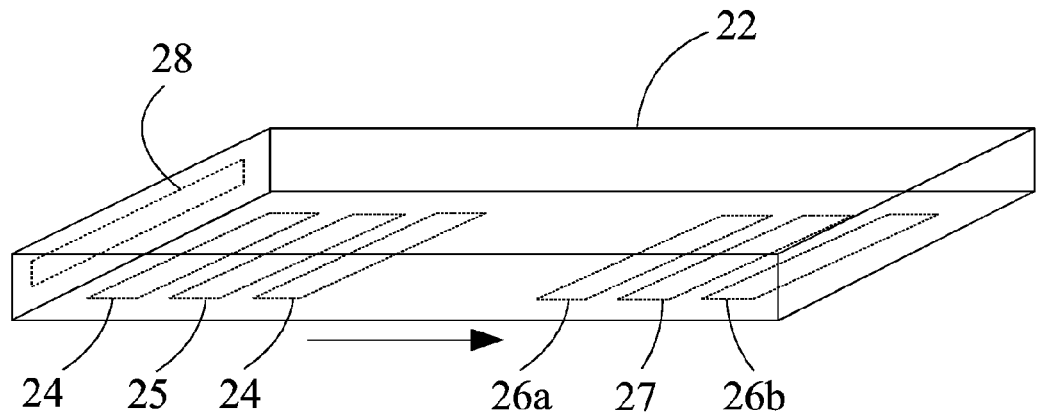
FIG. 8 is a perspective view of the separation device of FIG. 7.

A second embodiment of a separation device 21 is shown schematically in FIGS. 7 and 8, being a side view and a perspective view, respectively. In principle, this embodiment is equivalent to the first embodiment but the flow streams have been extended to a greater height/width necessitating a modification of the placement of the ultrasonic transmitters and the inlets and outlets. A flow channel 22, top and bottom ultrasonic transmitters 23a and 23b, inlets 24 and 25, and outlets 26ab and 27 are shown. In this embodiment the ultrasonic standing wave is generated between the top and bottom walls, transverse to the flow direction. At the fundamental frequency, the ultrasonic standing wave will have a pressure node along a horizontal centre line between the side walls as shown to the left in FIG. 7. At the second order harmonic frequency, the ultrasonic standing wave will have two horizontal pressure nodes as shown to the right in FIG. 7. The working principle is the same as in the first embodiment, but with a different arrangement of the flows. Due to the laminar properties of the flows, the inlets may be arranged in a row after each other. Consecutive inlets are provided in the bottom. A fluid with a mix of particles is inserted through a pair of inlets 24 and pure medium is inserted through a central inlet 25.

Similarly to the first embodiment, the different sets of particles are collected at the respective pressure nodes, but here in top and bottom horizontal flow sheets (assuming a horizontal position of the device) and one central horizontal flow sheet. The top and bottom horizontal flow sheets correspond to the lateral flow channels of the first embodiment. Also the outlets may be arranged in a row after each other. Consecutive outlets are provided in the bottom. The first outlet 26a collects the first set of particles from the bottom horizontal flow sheet, the second outlet 27 collects the second set of particles from the central horizontal flow sheet, and the third outlet 26b collects the first set of particles from the top horizontal flow sheet.

The inlets and outlets may also be arranged in the front and rear vertical walls of the chamber.

Figure 9:
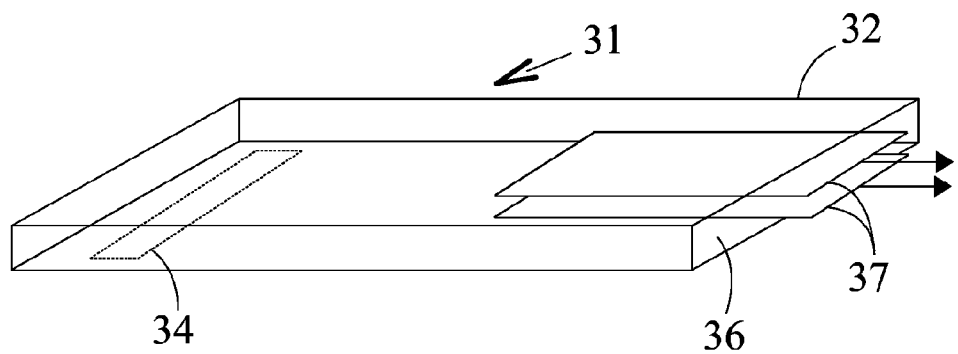
FIG. 9 is a perspective view of a preseparation device.

FIG. 9 illustrates a preseparation device 31 in which the particles are formed into two streams 37 by subjecting the preseparation chamber to a continuous second order harmonic standing wave having lateral pressure nodes. A fluid with a mix of particles is inserted through an inlet 34. The particle mix is gradually formed into two streams 37, both containing the same particle mix. The two streams 37 are delivered through a common outlet 36 e.g. to a common inlet 28 of the separation chamber 22 as shown in FIG. 8. The fluid mix contains a sufficient quantity of fluid to form central stream of particle-free fluid in the centre of the separation chamber 22. Note that dimensions of the preseparation chamber 32 are selected so that the resonance frequencies of the preseparation chamber 32 are not the same as the resonance frequencies of the resonance separation chamber 22, since this could disturb the function.

To enhance the performance of the method, a number of separations may be performed through a number of channels connected in series or an assembly comprising separation devices connected in series, so that one set of particles separated in one step is subjected to at least one further separation. The further separation may be performed using the same or different duty cycles, that is durations t1 and t2, and/or different amplitudes a1 and a2. For instance, one set of particles may be subjected to a further identical separation. This will result in a higher purity. Also, one set of particles may be subjected to a further different separation in order to divide the set of particles into further finely separated groups of particles.

An identical separation may be obtained in a chamber without flow. Then the supply of a particle mixture and removal of separated particles are performed through inlets and outlets located at suitable positions in the chamber or by means of pipetting.

EXAMPLE

A separation channel (385 µm wide and 250 µm deep) was etched into a <100> silicon wafer using anisotropic wet etching. The channel was sealed with a glass lid by anodic bonding and silicone tubes were glued to the inlets and outlets on the backside. The ultrasonic excitation (2 Mhz and 4 Mhz) was accomplished by attaching two piezoceramic crystals, one from the back side and one from the front side, with ultrasonic gel. The flow was controlled using three syringe pumps, 26 µl/min at the water inlet, 15 µl/min at the centre outlet and 75 µl/min at the side outlets. The balancing flow, 64 µl/min of particle solution, was self-drawn from an open cup. The particle solution consisted of a mix of 3 µm polystyrene beads, with a density of 1.05 g/cm$^3$, and 8 µm polymethylmethacrylate beads, with a density of 1.19 g/cm$^3$, suspended in $H_2O$. In order to get proper separation, the switching parameters had to be tuned correctly. This was done by systematically adjusting the parameters until sufficient visual separation was achieved. A typical operating cycle was 2 MHz for 800 µs and 4 MHz for 200 µs.

The present invention makes it possible to use this harmonic acoustic wave switching to separate suspended particles with different physical properties from each other. One application of this can be to separate different types of cells or bacteria from each other. Other possible applications include separation of different blood components.

The invention claimed is:

1. A method for separation of particles of a particle mixture suspended in a medium, comprising the steps of:
    subjecting medium in a chamber to ultrasonic energy generating a first ultrasonic standing wave at a first frequency having first pressure nodes;
    placing the particle mixture in the chamber, so that a concentration of the particle mixture is placed at or in the vicinity of a first pressure node of the ultrasonic standing wave at said first frequency or anywhere between the first pressure node and a wall of the chamber (2;22), wherein the medium and the suspended particle mixture are brought to flow in a laminar flow through a channel comprising the chamber and the ultrasonic standing wave is transverse to the flow direction;
    switching the frequency of the ultrasonic standing wave to a second frequency generating a second ultrasonic standing wave having at least one second pressure node, so that a first set of particles of the particle mixture is experiencing a smaller acceleration towards said second pressure node, and a second set of particles of the particle mixture is experiencing a greater acceleration towards said second pressure node;
    maintaining the second frequency during a time duration t2 and with an amplitude a2, allowing the first set of particles of the particle mixture to travel a smaller first distance, and the second set of particles of the particle mixture to travel a greater second distance;
    switching back to the first frequency; wherein the smaller first distance is so small that the first set of particles of the particle mixture is experiencing a greater acceleration towards the first pressure node, and the greater second distance is so great that the second set of particles of the particle mixture is experiencing a smaller acceleration towards the first pressure node;
    maintaining the first frequency during a time duration t1 and with an amplitude a1, allowing the first set of particles of the particle mixture to travel back towards the first pressure node, while the second set of particles of the particle mixture is not allowed to travel a significant distance; and
    repeatedly switching the ultrasonic standing waves between the first and second frequencies with a duty cycle involving their respective time durations t1 and t2, and amplitudes a1 and a2, so that a substantial part of the first set of particles of the particle mixture is collected at the first pressure node, and a substantial part of the second set of particles of the particle mixture is collected at the second pressure node.

2. A separation method according to claim 1, wherein said first frequency is a second order harmonic frequency of the chamber, and said second frequency is a fundamental frequency of the chamber.

3. A separation method according to claim 1, wherein the amplitudes a1 and a2 of the first and second frequencies are maintained fixed, and the durations t1 and t2 of the first and second frequencies are varied.

4. A separation method according to claim 1, wherein the durations t1 and t2 of the first and second frequencies are maintained fixed, and the amplitudes a1 and a2 of the first and second frequencies are varied.

5. A separation method according to any one of claims 1, 3 or 4, wherein the concentration of the particle mixture is supplied at two sides of the channel, while pure medium is supplied at the centre of the channel, and the first set of particles is collected at two lateral channel exits, while the second set of particles is collected at a central channel exit.

6. A separation method according to claim 5, wherein the said first frequency is 4 MHz and said second frequency is 2 MHz, the duration t1 of the first frequency is 200 µs and the duration t2 of the second frequency is 800 µs for a separation channel 385 µm wide and 250 µm deep.

7. A separation method according to any one of claims 1, 3 or 4, wherein the first and second set of particles are collected at consecutive outlets in the bottom of the channel.

8. A separation method according to any one of claims 1, 3 or 4, wherein a number of separations are performed through a number of channels connected in series, so that one set of particles separated in one step is subjected to at least one further separation.

9. A separation method according to claim 8, wherein the further separation is performed using different durations t1 and t2 and/or amplitudes a1 and a2.

* * * * *